United States Patent

Sher et al.

[11] 4,364,381
[45] Dec. 21, 1982

[54] SURGICAL CLAMP AND DRILL-GUIDING INSTRUMENT

[76] Inventors: Jay H. Sher, 19 Vermeer Dr., Apt. 8, South Amboy, N.J. 08879; A. Norman Cranin, 209 Cedar Ave., Hewlett, N.Y. 11557

[21] Appl. No.: 117,183

[22] Filed: Jan. 31, 1980

[51] Int. Cl.³ .............................................. A61F 5/04
[52] U.S. Cl. .............................. 128/92 E; 128/92 EA; 128/92 EB
[58] Field of Search ............ 128/92 R, 92 E, 92 EB, 128/92 EA; 408/72 B, 104, 105, 107, 108, 115 R, 115 B, 241 B; 269/166, 169, 170, 268, 269, 270, 87.1, 87.2, 87.3

[56] References Cited

U.S. PATENT DOCUMENTS

| | | | |
|---|---|---|---|
| 1,556,421 | 10/1925 | Chayes . | |
| 2,014,289 | 9/1935 | Page | 33/174 |
| 2,061,217 | 11/1936 | Watcher | 269/170 |
| 2,181,746 | 11/1939 | Siebrandt | 128/83 |
| 2,291,413 | 7/1942 | Siebrandt | 128/83 |
| 2,576,801 | 11/1951 | Michael | 269/87.2 |
| 2,653,820 | 9/1953 | Schade | 408/105 |
| 2,815,778 | 12/1957 | Holman | 269/170 |
| 3,562,912 | 2/1971 | Edelman | 32/40 |
| 3,674,375 | 7/1972 | Reed et al. | 408/115 |
| 3,690,005 | 9/1972 | Edelman | 32/40 |
| 3,727,611 | 4/1973 | Schultz | 128/92 EB |
| 3,835,849 | 9/1974 | McGuire | 128/92 EB |
| 3,867,932 | 2/1975 | Huene | 128/92 EB |

*Primary Examiner*—Stephen C. Pellegrino
*Assistant Examiner*—C. W. Shedd
*Attorney, Agent, or Firm*—Blum, Kaplan, Friedman, Silberman & Beran

[57] ABSTRACT

A surgical clamping and drill-guiding instrument for aiding in the placement of transosteal implants is provided. The instrument includes an L-shaped lower member having a horizontal screw receiving portion for receiving a screw with a rotatable wing portion thereon, and a keyed upright. An upper locking member is positioned on the keyed upright for placing the instrument on the gingival crest by pinching a spring along the keyed upright. The instrument is secured in position by tightening the screw which drives the wings into the lower surface of the mandible for providing a vise-like grip. The screw is provided with a central opening for receiving drill guide inserts of varying sizes for drilling through the mandible. The instrument may be placed in as many positions as transosteal implants are necessary.

11 Claims, 10 Drawing Figures

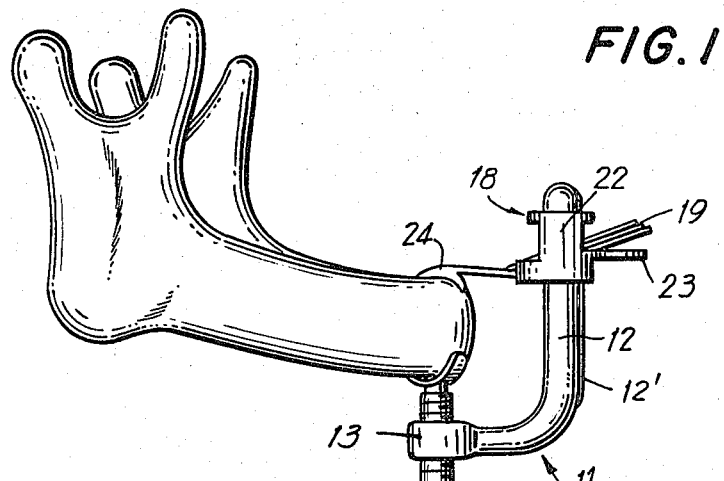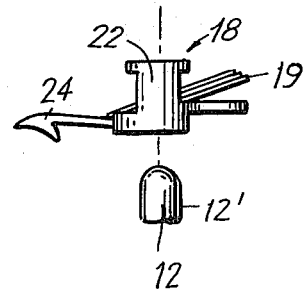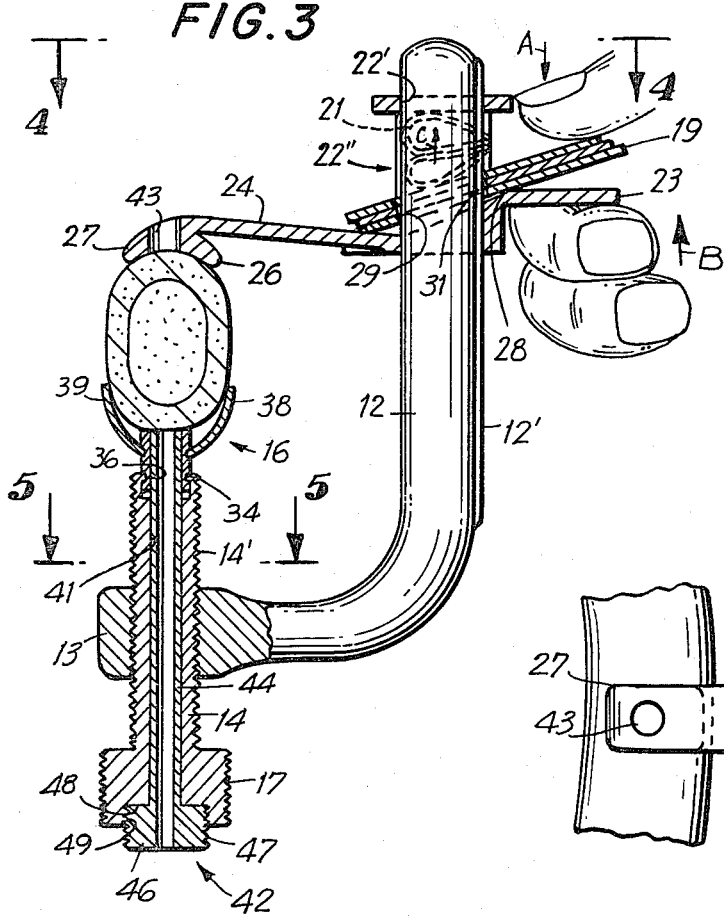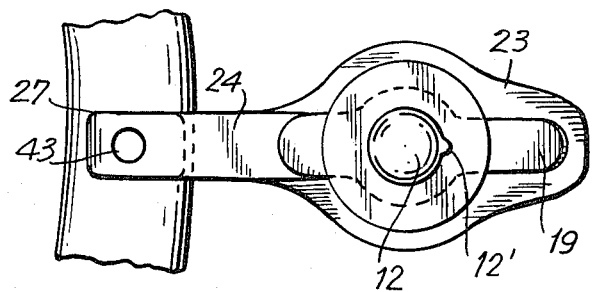

FIG. 7
FIG. 8
FIG. 6
FIG. 9
FIG. 5
FIG. 10
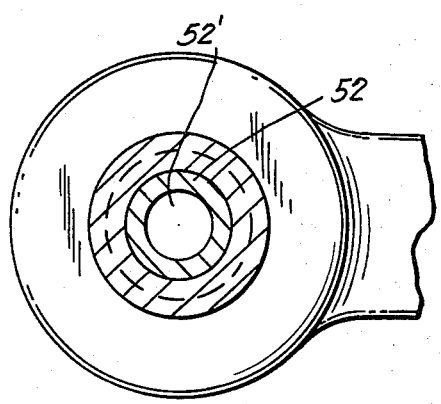
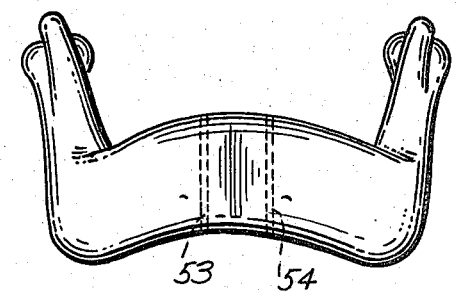
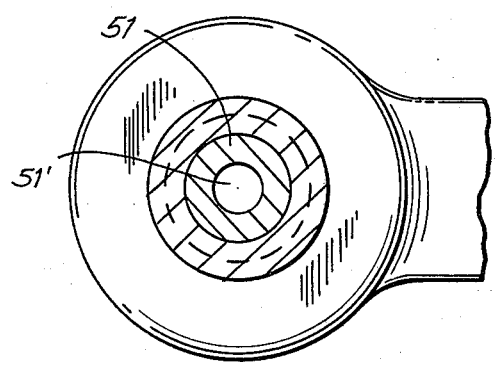
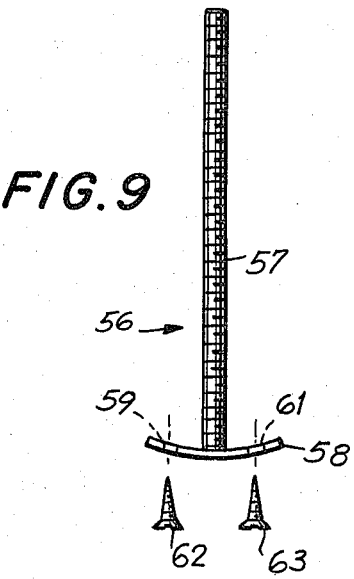
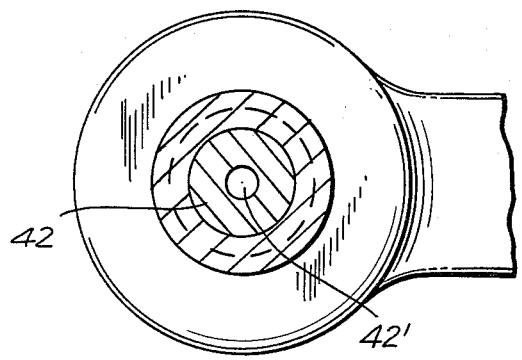
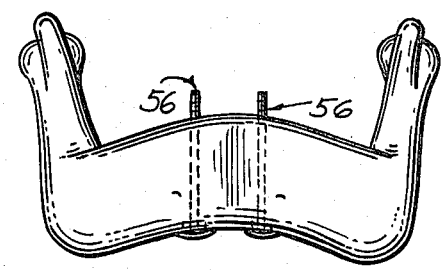

SURGICAL CLAMP AND DRILL-GUIDING INSTRUMENT

BACKGROUND OF THE INVENTION

This invention relates generally to a surgical instrument, and more particularly to a surgical clamping and drill-guiding instrument for positioning transosteal implants.

Surgical instruments for assisting in placement of transosteal implants are not generally available. When positioning a dental prosthesis on the mandible, it is often desirable to utilize an anchoring device inserted through the mandible from the inferior border for holding the dental prosthesis or subperiosteal implant on the crest of the mandible. In such cases a small submental skin incision and dissection in order to expose the inferior of the mandible is made. A pilot drill hole need be made through the mandible from the inferior border to the gingival crest intraorally. In order to complete this pilot drill hole, it is desirable to have a surgical clamping and drill-guiding instrument for securing the position of the drill and for guiding the drill through the mandible.

SUMMARY OF THE INVENTION

Generally speaking, in accordance with the invention, the surgical clamping and drill-guiding assembly for aiding in the placement of transosteal implants for the mandible is provided. The assembly is shaped like a C-clamp and includes a curved lower member having a keyed upright portion and a horizontal screw receiving portion which is to be positioned opposite the inferior surface of the mandible. The screw receiving portion receives a screw having a pair of wings rotatably mounted thereon. An upper locking member is positioned on the keyed upright portion with an extending arm for engaging the gingival crest. The upper member is displaceable and is locked on the upright portion by pinching a spring and slat assembly.

When the assembly has been placed in its appropriate position, it is secured to the mandible by tightening the screw which drives the wings into the lower surface of the mandible for providing a vise-like grip. The screw is provided with a longitudinal opening for receiving inserts for receiving drills of various sizes for drilling holes of a desired diameter through the mandible. The drilling is performed by a small diameter drill which is then increased to the necessary size. The assembly is placed in as many positions along the mandible as transosteal implants are necessary.

Accordingly, it is an object of the invention to provide an improved surgical instrument.

Another object of the invention is to provide an improved surgical instrument for placement of a transosteal implant.

A further object of the invention is to provide an improved surgical clamping and drill-guiding instrument.

Still another object of the invention is to provide an improved surgical clamping and drill-guiding instrument suitable to receive drill-guides of varying sizes.

Another object of the invention is to provide an improved surgical instrument for aiding in the placement of a transosteal implant and receive drill guides of various sizes.

Still another objects and advantages of the invention will in part be obvious and will in part be apparent from the specification.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a surgical instrument constructed and arranged in accordance with the invention shown in engagement with a mandible;

FIG. 2 is a partial exploded perspective illustrating the individual members of the instrument depicted in FIG. 1;

FIG. 3 is a cross-sectional view of the instrument depicted in FIG. 1;

FIG. 4 is a top plan view of the instrument taken along line 4—4 of FIG. 3;

FIG. 5 is a partial sectional view of the screw member of the instrument taken along line 5—5 of FIG. 3;

FIG. 6 is a partial sectional view of the screw member of FIG. 5 having a smaller diameter drill guide therein;

FIG. 7 is a partial sectional view of the screw member of FIG. 5 having another drill guide member therein;

FIG. 8 is a front view of a mandible having two pilot holes drilled therethrough;

FIG. 9 is a plan view of a transosteal implant and anchoring screws; and

FIG. 10 is a front view of the mandible illustrating two transosteal implants secured in the pilot holes.

DESCRIPTION OF THE PREFERRED EMBODIMENTS

Referring now to FIG. 1, a surgical clamping and drill-guiding instrument constructed and arranged in accordance with the invention is shown generally as 10. Instrument 10 is generally shaped in the form of a C-clamp and is shown clamped about a mandible. Instrument 10 includes a curved lower portion 11 and an upright post 12 having a key 12'. Curved lower portion 11 includes a ring 13 having a threaded opening 13' for receiving an elongated clamping screw 14 having thread 14' and a clamping wing 16 rotatably mounted at the upper portion thereof. A knurled turning ring 17 is fixably mounted at the lower portion of elongated clamping screw 14.

Surgical instrument 10 is completed with an upper locking member 18 which is displaceable along the keyed upright post 12 and may be locked at any position therealong by a series of slats 19 and an internal spring 21 shown more clearly in the cross-section in FIG. 3. Upper locking member 18 includes a central body portion 22 having an opening 22' therethrough dimensioned to fit about keyed upright post 12 and a transverse opening 22" to receive slats 19. A horizontal extending gripping region 23 for releasing the locking engagement between slats 19 and post 12. Upper locking member 18 includes an upper vise arm 24 which extends from central body portion 22 to the superior surface of the mandible for gripping the mandible by a pair of finger regions including a front finger 26 and a rear finger 27 in cooperation with clamp wing 16.

Referring now to the exploded perspective view of FIG. 2, displacement of upper locking member 18 along the full length of keyed upright post 12 for removing upper member 18 is shown. Slats 19 are formed with a central opening 29 having an additional notch 31 for fitting about key 12' keyed upright post 12. In order to displace locking member 18 along keyed upright post 12, slats 19 are pinched and displaced in the manner illustrated in FIG. 3.

Referring now to FIG. 3, slats 19 are displaced by placing the thumb above slats 19 and the index finger below gripping region 23 for pivoting about a point 28 for biasing against spring 21. When slats 19 are pivoted about point 28 the engagement between opening 29 and keyed upright post 12 is released thereby freeing upper locking member 18 to permit removal as shown in FIG. 2. Slats 19 are pivoted about point 28 by pressing downwardly in arrow direction A with the thumb pressing upwardly in arrow direction B with the index finger against gripping portion 23. This pivots slats 19 about point 28 biasing spring 21 in direction of arrow C against the upper region of central body portion 22 as shown in FIG. 3.

The details of construction of screw receiving ring 13 and screw 14 are shown in the cross-sectional region in FIG. 3. Ring 13 is formed with an internal thread 32 for receiving screw 14 formed with an outer mating threaded surface 33 which extends most of the length of screw 14. The upper region of screw 14 is formed with an inwardly facing flange 34 for mating with a recess 36 for rotatably mounting a washer 37 on which is mounted wing 16. Wing 16 includes a frong finger 38 and a rear finger 39 for gripping the inferior surface of the mandible. As shown in FIG. 3, screw 14 and washer 37 are formed with a central opening 41 for receipt of a drill guide 42 which has a longitudinal opening 42' as will be described in more detail below. A cooperating drill opening 43 is formed in a locking member arm 24 between front finger 26 and rear finger 27.

As shown in FIG. 3, drill guide 42 includes an elongated hollow cylindrical region 44 for insertion into opening 41 of screw 14 and includes a cylindrical base 46 with an external thread 47. The base of screw 14 at knurled region 17 is formed with an enlarged opening 48 with an internal thread 49 for cooperating with base 46. Drill guide 42 is formed with drill opening 42' which may be of varying size for accomodating drills of varying sizes.

Referring now to FIGS. 5–7, ring 13 is shown supporting a series of drill guides having various openings. For example, when surgical instrument 10 is utilized a first insert 42 having a 3/64 diameter opening 42' is utilized so that the first smallest drill bit will rotate through the guide and bone in the desired path. After this pilot hole is completed, a second insert 51 having a 5/64 inch opening 51' is utilized, and finally, a third insert 52 having a 7/64 diameter opening 52' is utilized.

With a drill guide of desired size positioned in screw 14, surgical instrument 10 is utilized as follows. A small submental skin incision and dissection to expose the inferior border of the mandible is made. At this time instrument 10 is directed through the incision and wing 16 is positioned along the inferior surface where the hole in the mandible for the transosteal implant is desired. Rear finger 39 and front finger 38 are positioned firmly against the bone and upper member 18 is positioned on the gingival crest by pinching slats 19 and sliding on keyed post 12. Upper member 18 is lowered on post 14 until front finger 26 and rear finger 27 on arm 24 firmly abut the superior surface of the mandible.

Once surgical instrument 10 is properly aligned in this manner, instrument 10 is secured in vise fashion by tightening screw 14 at knurled turning ring 17. As screw 14 is tightened, front finger 38 and rear finger 39 on ring 16 are urged against the mandible for a vise-like grip of the mandible. When the desired holes in the mandible are drilled as illustrated in FIG. 8 at 53 and 54, instrument 10 is removed. At this time a transosteal implant 56, as shown in FIG. 9, is inserted into openings 53 and 54. Transosteal implant 56 includes an elongated region 57 which may be threaded or formed with a roughened engagement surface and a saddle shaped border cap 58. Border cap 58 is formed with openings 59 and 61 for receipt of screws 62 and 63 for securing implant 56 into the mandible as illustrated in FIG. 10. Screws 62 and 63 may be 7 mm screws for securing border cap 58 to the inferior region of the mandible. Surgical instrument 0 can facilitate placement of as many transosteal implants as necessary to support a full lower or a partial denture with excellent stability.

Accordingly, by constructing and arranging the surgical clamping and drill-guiding assembly in this manner, multiple holes of a desired size may be drilled in the mandible. The elongated drill guide provides means for aligning the drill for accurate location of the openings. Additional convenience and speed of operation is attained by the ability to change drill guide sizes without removing the instrument from the mandible.

It will thus be seen that the objects set forth above, and those made apparent from the preceding description, are efficiently attainded and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein describe, and all statements of the scope of the invention which, as a matter of language, might be said to fall therebetween.

What is claimed is:

1. A surgical clamping and drill-guiding instrument for gripping a bone exposed during surgery and providing an accurate drill guide comprising:

an L-shaped member having an elongated keyed post and a leg extending from the post, the leg having a screw receiving portion for positioning on one side of the bone to be gripped;

an elongated clamping screw having a longitudinal opening means therethrough for receiving a removable drill guide of a chosen size for guiding a drill of said chosen size for drilling into the bone, and a clamping member rotatably mounted about said opening means at the engagement end of said screw facing the bone, said clamping screw being engageably disposed in said screw receiving portion; and a central body portion with an opening for receipt of said post and being displaceable along said post; an arm extending from said body portion generally parallel to said leg, said arm including fingers for engaging the outer side of the bone and having an opening between said fingers for cooperating with the opening means in said screw and locking means for locking the body portion at a preselected position on said post; said post, when received within and being in movable keyed engagement with said body portion, provides an alignment means which facilitates the cooperation of the opening means in said screw with the opening between said fingers;

said screw and clamping member displaceable through said screw receiving portion on said leg towards the bone so as to fixedly locate said drill guide with respect to the bone disposed between said clamping member and said fingers on the arm for providing a vise-like grip about the bone.

2. The surgical clamping and drill-guiding instrument of claim 1, wherein said drill guide means is an elongated cylindrical member having a longitudinal opening for positioning in said clamping screw.

3. The surgical clamping and drill-guiding instrument of claim 2, wherein said clamping screw has an enlarged threaded opening for receiving said drill guide and said drill guide is formed with an enlarged cylindrical base having an external threaded region for securing said drill guide into said clamping screw.

4. The surgical clamping and drill-guiding instrument of claim 1, wherein said post is substantially cylindrical with a keyed region for aligning said upper locking member.

5. The surgical clamping and drill-guiding instrument of claim 4, wherein said locking means includes a plurality of locking slats formed with an opening for engaging said post when said slats are at an oblique angle to said post.

6. The surgical clamping and drill-guiding instrument of claim 5, including biasing means for maintaining said slats at an oblique angle to said post.

7. The surgical clamping and drill-guiding instrument of claim 6, wherein said biasing means is a spring disposed in said body portion.

8. The surgical clamping and drill-guiding instrument of claim 1, wherein said lower member is integrally formed in an L-shape with said engaging means on the shorter leg of said L.

9. The surgical clamping and drill-guiding instrument of claim 7, wherein said slats include a groove for cooperating with said key.

10. The surgical clamping and drill-guiding instrument of claim 1, wherein said clamping member is wing shaped with a front and a rear finger for positioning about a bone disposed in said instrument.

11. The surgical clamp and drill-guiding instrument of claim 1 wherein said locking means includes three locking slats through said upper locking member and about said post, said slats biased towards an oblique angle to said post for engaging said post and fixing the position of said post at a preselected position.

* * * * *